United States Patent
Ohashi et al.

(10) Patent No.: US 8,045,151 B2
(45) Date of Patent: Oct. 25, 2011

(54) LAMINATED FILM DEFECT INSPECTION METHOD AND LAMINATED FILM DEFECT INSPECTION DEVICE

(75) Inventors: Hiromichi Ohashi, Ibaraki (JP); Kosuke Sato, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 318 days.

(21) Appl. No.: 12/376,276

(22) PCT Filed: Aug. 12, 2008

(86) PCT No.: PCT/JP2008/064484
§ 371 (c)(1),
(2), (4) Date: Feb. 3, 2009

(87) PCT Pub. No.: WO2009/025210
PCT Pub. Date: Feb. 26, 2009

(65) Prior Publication Data
US 2010/0165333 A1 Jul. 1, 2010

(30) Foreign Application Priority Data

Aug. 23, 2007 (JP) ................................. 2007-217251
Aug. 11, 2008 (JP) ................................. 2008-207125

(51) Int. Cl.
*G01N 21/00* (2006.01)
(52) U.S. Cl. ................... 356/239.2; 356/239.7
(58) Field of Classification Search .... 356/237.1–237.6, 356/238.1–238.3, 239.1–239.8; 156/378–379, 156/508–510, 267–268, 190–192, 60–64
See application file for complete search history.

(56) References Cited

U.S. PATENT DOCUMENTS

| | | | | |
|---|---|---|---|---|
| 6,030,474 A | * | 2/2000 | Isono et al. | ...... 156/64 |
| 2007/0284759 A1 | * | 12/2007 | Suguro et al. | ...... 257/783 |

FOREIGN PATENT DOCUMENTS

| | | |
|---|---|---|
| JP | 05-107149 A | 4/1993 |
| JP | 08-113422 A | 5/1996 |
| JP | 08-300489 A | 11/1996 |
| JP | 2003-149164 A | 5/2003 |
| JP | 2003-231214 A | 8/2003 |
| JP | 2004-029204 A | 1/2004 |
| JP | 2004-149293 A | 5/2004 |
| JP | 2007-076106 A | 3/2007 |
| WO | WO-2008/047712 A1 | 4/2008 |

OTHER PUBLICATIONS

International Search Report for the Application No. PCT/JP2008/064484 mailed Oct. 7, 2008.

* cited by examiner

*Primary Examiner* — Tri T Ton
(74) *Attorney, Agent, or Firm* — Cheng Law Group, PLLC

(57) ABSTRACT

A first inspection process of inspecting presence of a defect on a front surface of a film body with a protective film separated therefrom; a separator removing process of separating a separator from the inspected laminated film; a second inspection process of inspecting presence of the defect in the film body in a vertical attitude while introducing the film body with the separator separated and removed therefrom to a film travel path directed in a vertical direction, and storing detection data; a separator laminating process and a protective film laminating process of laminating a separator and a protective film to a back surface and a front surface of the inspected film body, respectively; and a film collecting process of winding up the inspected laminated film laminated with the protective film and the separator are provided.

13 Claims, 6 Drawing Sheets

LAMINATED FILM DEFECT INSPECTION METHOD AND LAMINATED FILM DEFECT INSPECTION DEVICE

TECHNICAL FIELD

The present invention relates to laminated film defect inspection method and device for inspecting defects such as defacement and damage of the laminated film used in a polarizing plate, a glass substrate, and the like of a liquid crystal display.

BACKGROUND ART

In the manufacturing step of the liquid crystal display, a step of fabricating a laminated optical film by laminating a sheet of thin film (polarizing plate) to a band-shaped function film (phase difference film) is used (see patent document 1).
[Patent document 1] Japanese Laid-Open Patent Publication No. 2007-76106

DISCLOSURE OF THE INVENTION

Problems to be Solved by the Invention

The sheet of film (polarizing plate) to be laminated to the band-shaped function film is formed as a laminated film by laminating a separator to an adhesive surface on the back side of a film body and laminating a protective film to a front surface of the film body. An original roll in which such long laminated film is wound in a roll is supplied to a punching and cutting step to be punched and cut into a sheet of film in a predetermined dimension.

The film body of the wounded laminated film sometimes has microscopic dust attached on the surface or the interior thereof, remaining thereon in a special shape (hereinafter appropriately referred to as "nick") as if twisted into a trace form biting foreign substances that generate optical distortion, or unevenness created in a film surface processing. The sheet of film needs to be obtained by punching and cutting so as not to include such defects. It is thus important to inspect the defects such as defacement and damage of the laminated film with reflective or transmissive optical device, and recognize the defect produced position.

In this case, the laminated film has the protective film and the separator laminated to the front and the back thereof, respectively, and thus oversight, false recognition, and the like of defects are generated due to transmissive failure by optical characteristics (birefringence etc.) of the protective film and the separator, and diffuse reflection of the surface, and detection may not be performed at a satisfactory accuracy.

If scratches etc. exist on the protective film and the separator, the relevant scratches may be falsely recognized as scratches of the film body.

The present invention has been made in view of such situations, and it is a main object of the present invention to provide a method and a device for inspecting defects of a laminated film capable of inspecting the defects in the wounded laminated film at a satisfactory accuracy.

Means for Solving the Problems

A first invention relates to a method for inspecting a defect of a wound up laminated film; the method including a laminated film feed-out step of feeding out from an original roll the laminated film in which a protective film on a front surface of a film body and a separator on an adhesive surface on a back side of the film body are laminated together; a separator separation step of making a separation surface of a separator face downward at least at a separation point before separating the separator from the laminated film while guiding the fed-out laminated film to a predetermined path; an inspection step of inspecting presence of the defect of the laminated film while transporting the laminated film with the separation surface of the separator facing downward, and storing inspection information in a storage device; a separator laminating step of laminating the separator to the separation surface with the separation surface of the separator of the inspected film body facing downward; and a laminated film collecting step of winding up the inspected laminated film in which the separator is laminated to the back surface of the film body to form an inspected original roll.

(Effect)

According to this method, the separator is separated from the adhesive surface on the back side of the laminated film fed out from the original roll, and the film body, which adhesive surface is exposed, is guided with the back surface thereof facing downward. The presence of defects such as attachment of foreign substances and nicks are appropriately inspected by an optical device in this process. The inspection information such as the detected defect produced position is stored in the storage device. When referring to the film body facing downward, this means that the adhesive surface does not face upward. Therefore, this includes transporting the film body in a perpendicular attitude.

In this case, even in an unlikely event that dust drops in an inspection processing space, the dust can be suppressed from attaching to the adhesive surface of the film body, with the back surface thereof facing downward.

Thereafter, the separator is laminated to the back surface of the inspected film body to restore the original laminated film, and such laminated film is wounded up and collected to thereby form an inspected original roll.

The attachment of dust to the separation surface of the separator can be avoided by shortening the exposure time of the separation surface of the separator. However, foreign substances other than dust, knick, or the like are present on the film, and different inspection methods, for example, a plurality of types of inspection steps such as transmissive type and reflective type needs to be performed in order to recognize the same at satisfactory accuracy. Thus, the exposure time of the separation surface of the separator inevitably becomes longer. Therefore, this method effectively functions when a plurality of inspection steps is required as mentioned above.

The inspection information obtained in the inspecting steps may be stored in a storage device or a host computer of a communication device so as to be used as information for avoiding the defect produced site in the subsequent processing steps and a punching step.

A second invention according to the first invention further includes a protective film separation step of separating the protective film from the laminated film; an inspection step of inspecting presence of the defect on the front surface of the film body while guiding the laminated film with the protective film separated therefrom to a predetermined film travel path, and storing inspection information in the storage device; and a protective film laminating step of laminating a protective film to a front surface of the inspected film body; wherein the laminated film collecting step includes winding up the inspected laminated film in which the protective film is laminated to the front surface of the film body and the separator is laminated to the back surface of the film body to form an inspected original roll.

(Effect)

According to this method, the protective film is separated from the laminated film fed out from the original roll, and the front surface of the film body is exposed. The presence of defects on the exposed surface of the film body is appropriately inspected by an optical device, and inspection information such as detected defect produced position is stored in the storage device.

The inspection information obtained in the inspecting step may be stored in a storage device or a host computer of a communication device and the like so as to be used as information for avoiding the defect produced site in the subsequent processing steps and punching step.

A third invention according the second invention further has a feature that the separator is separated from the back surface of the film body and inspection is performed after separating the protective film from the film body and inspecting the resulting protective film; and the laminated film is wounded up to form an inspected original roll after laminating the protective film and the separator to the front surface and the back surface of the inspected film body, respectively.

(Effect)

According to this method, the exposure time of the adhesive surface of the film can be reduced. Therefore, the attachment of dust to the adhesive surface can be more effectively suppressed.

A fourth invention according to the second invention further includes a marking step of marking the defect detected site of the film body after the inspection step of the film body with the protective film separated therefrom.

(Effect)

According to this method, the defect produced site in the film body can be easily visually recognized, and visual inspection and the like in the subsequent steps are facilitated.

A fifth invention according to any one of the second to the fourth inventions further includes a data recording step of providing position data of a detected defect site to an appropriate location on the front surface or the back surface of the inspected laminated film after at least either the separator laminating step or the protective film laminating step.

(Effect)

According to this method, inspection data is recorded for every original roll subjected to the inspection process, and the inspection data for every original roll is read using an appropriate reader in the subsequent steps so that a process avoiding the use of the defect produced site can be suitably performed.

A sixth invention according to any one of the second to the fifth inventions performs at least a second inspection process in a clean room.

(Effect)

According to this method, the film body with the protective film and the separator separated therefrom, and the front and back are exposed can be accurately inspected in a clean state. In other words, inspection can be performed at a satisfactory accuracy with the optical characteristics of the protective film and the like eliminated.

A seventh invention according to the sixth invention scavenges the clean room with the front surface side of the film as an upstream side of an air flow with respect to the film body traveling in a vertical attitude.

(Effect)

According to this method, even in an unlikely event dust of scavenging air flow exists, the possibility of contacting the adhesive surface on the back side of the film body is eliminated, and defacement during the inspection can be avoided in advance.

An eighth invention relates to a device for inspecting a defect of a laminated film that inspects a defect of a wound up laminated film, the defect inspection device including a laminated film supply device for supplying a laminated film in which a protective film on a front surface of a film body and a separator on an adhesive surface on a back side of the film body are laminated together; a separator separation device for separating the separator from the laminated film while introducing the laminated film fed out from the laminated film supply device to a predetermined path; an inspection device for making a separation surface of a separator face downward at least at the separation point of the separator, and inspecting presence of the defect while maintaining this state and transporting; a storage device for storing information of the inspection result; a separator supply device for feeding out a separator to a back surface of the film body; a separator laminating device for laminating the separator fed out from the separator supply device to the separation surface with the separation surface of the separator of the inspected film body facing downward; and a laminated film collecting device for winding up the inspected laminated film in which the separator is laminated to the back surface of the film body.

(Effect)

According to this configuration, the first invention can be suitably performed.

In the above configuration, preferably included are a protective film separation device for separating the protective film from the laminated film; an inspection device for inspecting presence of the defect at the front surface of the film body while introducing the laminated film with the protective film separated therefrom to a predetermined film travel path; a storage device for storing information of the inspection result; a protective film supply device for feeding out a protective film to the front surface of the film body; and a protective film laminating device for laminating the protective film fed out from the protective film supply device to the front surface of the inspected film body.

According to this configuration, defects are detected with the optical characteristics of the protective film and the separator separated from the film body eliminated. Therefore, the detection accuracy of defects can be enhanced.

According to the above configuration, the following configuration may be provided.

For instance, the device includes a marking device for marking a defect detected site of the film body based on the inspection result after separating of the protective film, and a data recording device for providing position data of the detected defect site to an appropriate location on the front surface or the back surface of the inspected laminated film after at least either the separator lamination or the protective lamination.

According to this configuration, the defect produced site of the film body can be easily visually recognized. The inspection data for every original roll can be read using an appropriate reader in the subsequent steps. Therefore, a process avoiding the use of the defect produced site can be suitably performed in the subsequent steps.

Effect of the Invention

According to the method and device for inspecting the defects of the laminated film the present invention described above, the defects in the wound up laminated film can be inspected at satisfactory accuracy, and the site where the defect is not produced can be used in the subsequent steps based on the information obtained by the inspection.

DESCRIPTION OF SYMBOLS 15 clean room
f film body
F laminated film (before inspection)
F' laminated film (after inspection)
p protective film
p' protective film
s separator
s' separator

BEST MODE FOR CARRYING OUT THE INVENTION

One embodiment of the present invention will be described below with reference to the drawings.

Figure 1:
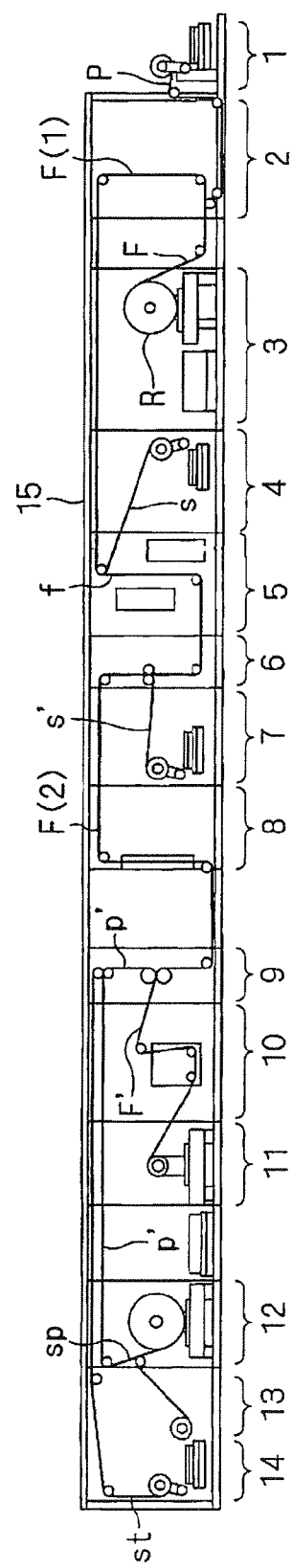
FIG. 1 is an overall side view of a defect inspection device.
Figure 2:
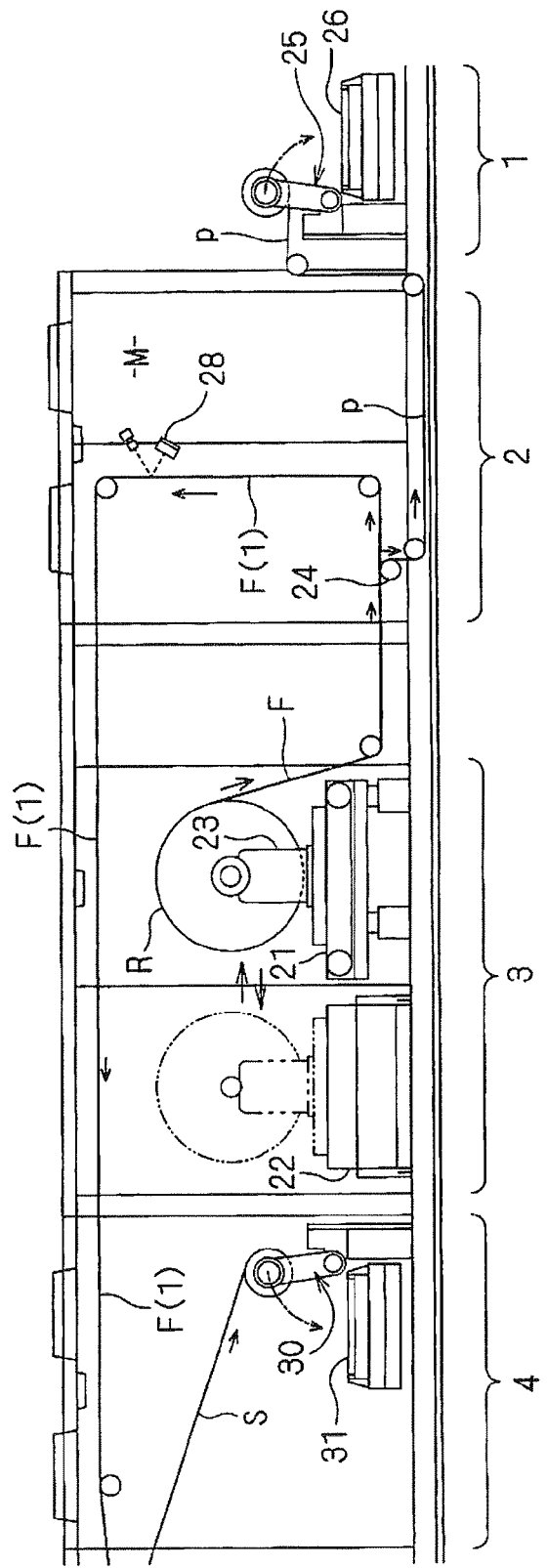
FIG. 2 is a side view showing one portion of a front end side of the defect inspection device.
Figure 3:
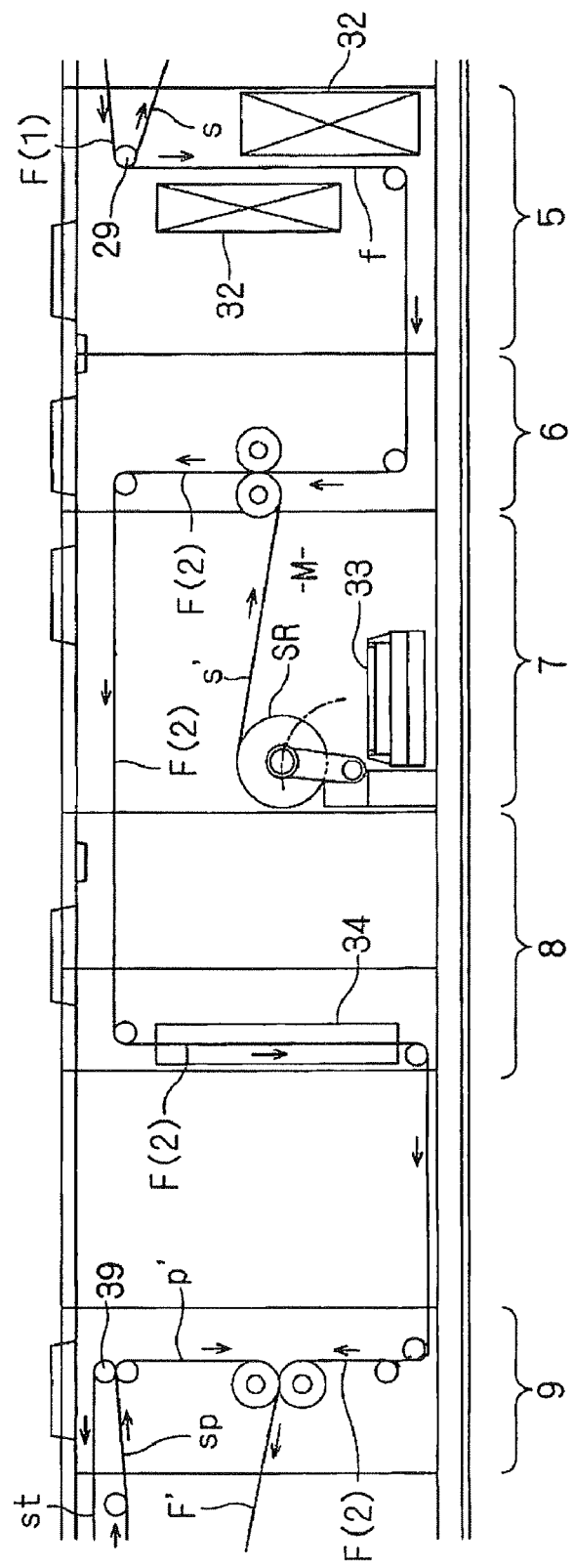
FIG. 3 is a side view showing an intermediate portion of the defect inspection device.
Figure 4:
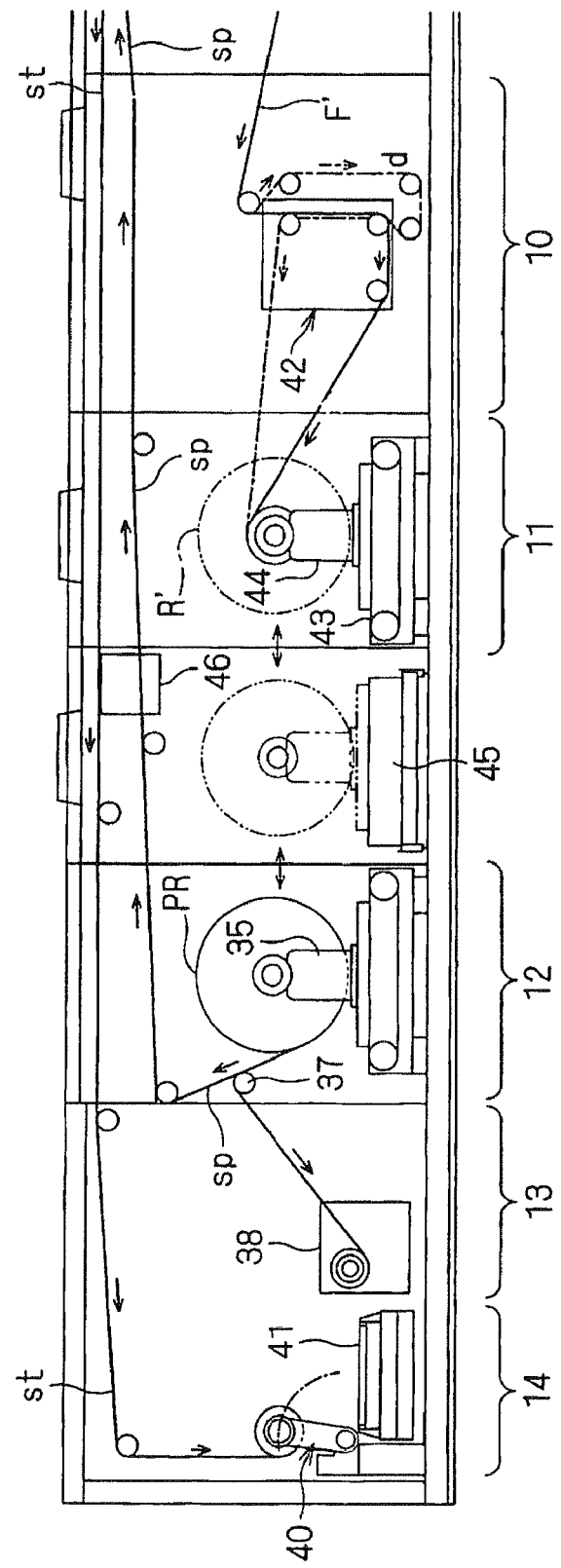
FIG. 4 is a side view showing one portion of a back end side of the defect inspection device.

FIG. 1 shows an entire defect inspection device for performing the method of the present invention, and FIG. 2 to FIG. 4 show each section of the defect inspection device in an enlarged manner. The defect inspection device has, in order from the right side of FIG. 1, a protective film collecting section 1, a first inspecting section 2, a laminated film supplying section 3, a separator collecting section 4, a second inspecting section 5, a separator laminating section 6, a separator supplying section 7, a marking processing section 8, a protective film laminating section 9, a data recordation processing section 10, a laminated film collecting section 11, a protective film supplying section 12, a protective film ear collecting section 13, and a separator collecting section for protective film 14 arranged in column, where each section other than the protective film collecting section 1 is arranged inside a clean room 15 that is forcibly scavenged.

The first inspecting section 2 corresponds to an inspection device after protective film separation of the present invention, the laminated film supplying section 3 corresponds to a laminated film supply device, the second inspecting section 5 corresponds to an inspection device after separation of the separator, the separator laminating section 6 corresponds to a separator laminating device, the separator supplying section 7 corresponds to a separator supply device, the marking processing section 8 corresponds to a marking device, the protective film laminating section 9 corresponds to a protective film laminating device, the data recordation processing section 10 corresponds to a data recording device, the laminated film collecting section 11 corresponds to a laminated film collecting device, and the protective film supplying section 12 corresponds to a protective film supply device.

Figure 6:
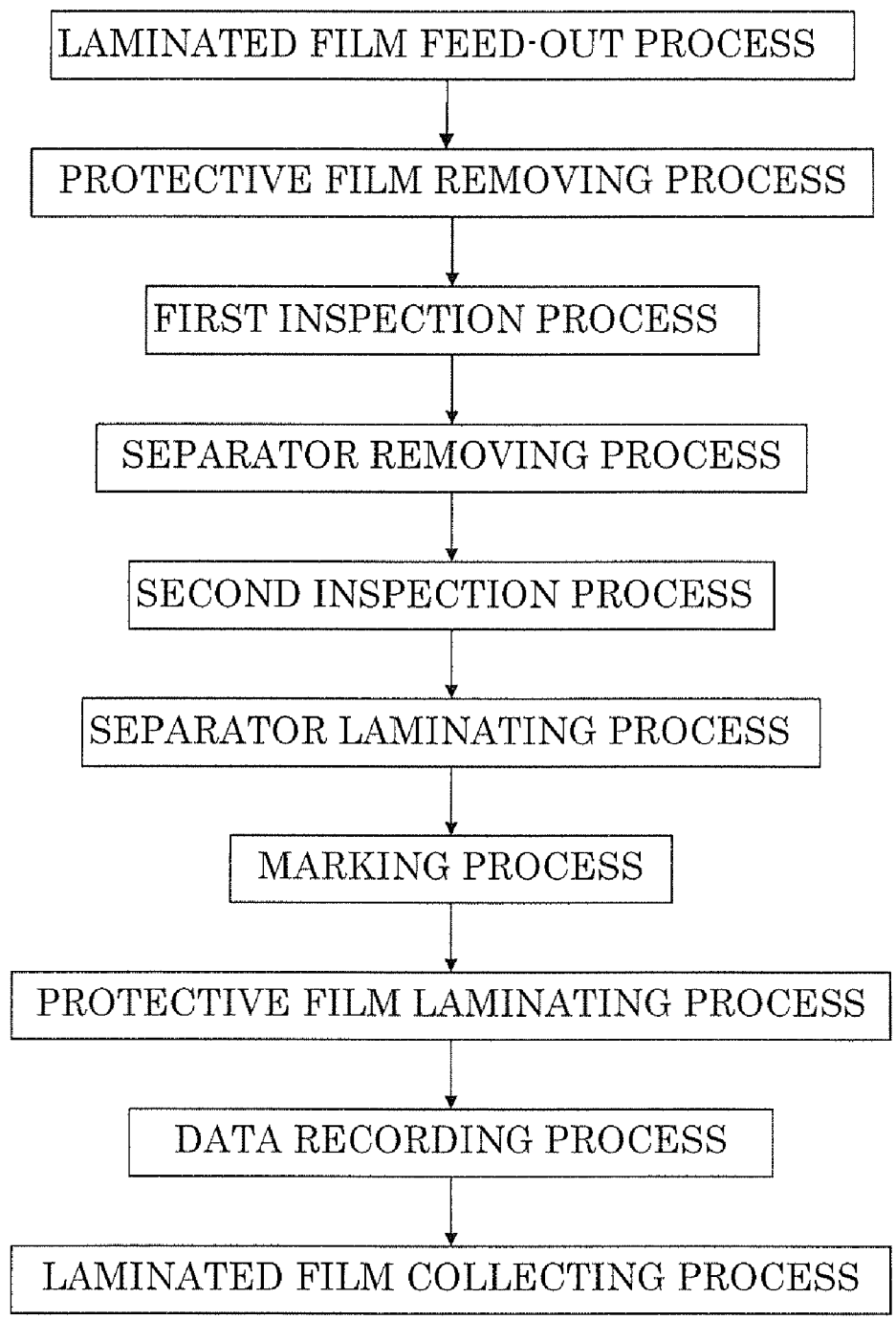
FIG. 6 is a flowchart showing the inspection process.

The laminated film inspection process performed using the defect inspection device is described based on the flowchart shown in FIG. 6.

[Laminated Film Feed-Out Process]

Figure 5:
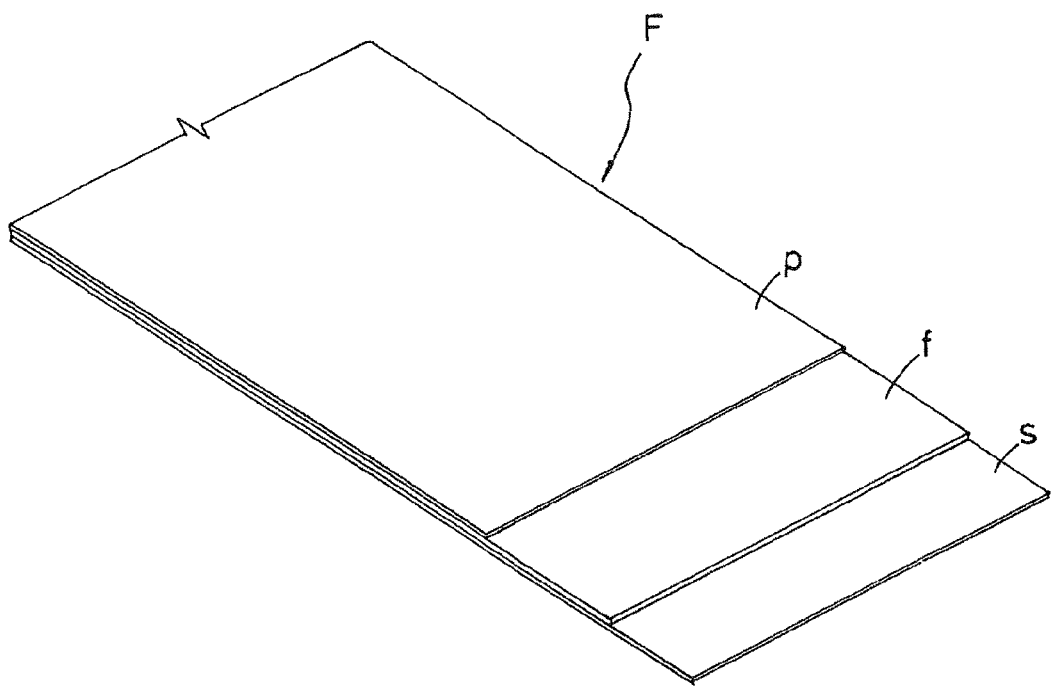
FIG. 5 is a perspective view showing one portion of the laminated film.

As shown in FIG. 2, a receiver base 21 and a conveyor 22 are arranged in the laminated film supplying section 3, and an original roll R carried in while being supported by a mount 23 is transferred and set by the conveyor 22 at a predetermined position on the receiver base 21. A laminated film F is fed out from the original roll R on the receiver base 21, and introduced to the first inspecting section 2 through a predetermined travel path. As shown in FIG. 5, the laminated film F has a laminated structure of three layers in which a protecting film p is laminated to a front surface of a film body f made from a polarizing film, and a separator s is laminated to an adhesive surface on the back side of the film body f.

[Protective Film Removing Process]

Returning to FIG. 2, the laminated film F is introduced to the lower part of the first inspecting section 2 in an attitude the protective film p faces downward, and the protective film p is separated and removed through a separation roller 24 arranged near the floor. The separated protective film p is introduced to the protective film collecting section 1, and then wounded up and collected by a windup device 25. The protective film p that is wound up and collected is transferred to a carry-out conveyor 26 and carried out.

[First Inspection Process]

The laminated film F(1) of two-layer structure in which the protective film p is separated and removed, and only the separator s is laminated is monitored by a CCD camera 28. In this process, inspections on the state of surface treatment such as antireflection coating of the exposed surface of the film body f, presence of foreign substance attachment, and the like are performed, and inspection data thereof is stored along with position data in the traveling direction at the film body f.

The first inspecting section 2 is arranged with a working space M where the worker can monitor the film travel path, so that visual inspection can be performed as necessary.

[Separator Removing Process]

The laminated film F(1) with the protective film p removed therefrom and subjected to the inspection in the first inspecting section 2 is moved above the laminated film supplying section 3 and the separator collecting section 4, and sent to the second inspecting section 5 shown in FIG. 3. A separation roller 29 is arranged at the upper part of the second inspecting section 5 so that the separator s is separated from the introduced laminated film F(1), where the separated separator s is introduced to the separator collecting section 4 shown in FIG. 2 and wounded up and collected by a windup device 30. The separator s that is wound up and collected is transferred to a carryout conveyor 31 and carried out.

[Second Inspection Process]

The film body f in which the separator s is separated and removed therefrom and front and back thereof are exposed is introduced to the lower side along a vertical path c at the same time as the separating. In the path c, a light transmissive (or reflective) monitoring device 32 acts on the film body f in the vertical attitude, and defect inspection of a nick, which is a defect in a special shape as if twisted into a trace form biting foreign substances that generate optical distortion occurring at the film body f, attachment of foreign substances, and the like is performed. For instance, defect inspection of foreign substances and lint, nicks, and luminescent spot is performed with the light transmissive monitoring device, and defect inspection of unevenness created by the attachment of adhesive foreign substances and air bubbles contained in the adhesive layer is performed with the reflective monitoring device. Such plurality of types of inspection data are stored along with the position data in the traveling direction at the film body f.

[Separator Laminating Process]

The film body f subjected to the inspection in the second inspecting section 5 is immediately introduced to the separator laminating section 6. A new supplied separator s' is laminated to the adhesive surface on the back side of the film body f while being transported and sandwiched between a right and left pair of a nip roller and a transportation roller. The separator s' is used that is fed out from a separator original roll SR installed in the separator supplying section 7. The separator original roll SR is transferred to a carry-in conveyor 33 and carried in.

That is, the adhesive surface of the film body f is not facing upward unless the separator s is separated from the film body f until a new separator s' is laminated.

[Marking Process]

The laminated film F(2) of a two-layer structure in which only the separator s' is laminated to the inspected film body f is passed through the upper part of the separator supplying section 7 and sent to the back side, and introduced to the marking processing section 8. The laminated film F(2) introduced to the marking processing section 8 is traveled and guided to the lower side in a perpendicular attitude, and a mark providing process is performed by a marking device 34.

An inkjet type of a plot type of the marking device 34 is used, where a mark indicating the defected site is provided on the outer surface of the separator s' based on the stored inspection data. In this case, marking can be performed by color coding according to the kinds of defects.

[Protective Film Laminating Process]

As shown in FIG. 3, the laminated film F(2) performed with the marking process is introduced to the protective film laminating section 9, and a new protective film p' supplied from the protective film supplying section 12 shown in FIG. 4 is laminated on the front surface of the film body f of the laminated film F(2).

In the protective film supplying section 12, the protective film original roll PR wounded with the protective film with the separator sp is supported by way of a mount 35. The protective film with the separator sp fed out from the protective film original roll PR is cut at both end sides (hereinafter appropriately referred to as "ear") of the film by a slitter 36, and the ears sp' at both ends of the protective film with the separator sp are inverted and guided by way of a guide roller 37, and wound up and collected by a windup device 38 of the protective film ear collecting section 13.

As shown in FIG. 4, the protective film with the separator sp cut off with the ears sp' at both ends and adjusted to a predetermined width is sent to the protective film laminating section 9 shown in FIG. 3 over the protective film supplying section 12, the laminated film collecting section 11, and the data recordation processing section 10, and a separator st is inverted and separated through a separation roller 39 arranged at the upper part of the protective film laminating section 9. The protective film p' immediately after the separator st is separated and removed is laminated on the front surface of the film body f of the laminated film F(2) supplied from the lower side by a nip roller. As shown in FIG. 4, the protective film with the separator sp with the ears sp' cut off at both ends is inserted to a dust removing device 46 equipped with a group of rollers, so that lint attached to and remaining at the cut ends of the protective film with separator sp is transferred and removed.

As shown in FIG. 4, the separated separator st is sent to the separator collecting section for protective film 14 through the upper side of the data recordation processing section 10, the laminated film collecting section 11, the protective film supplying section 12, and the protective film ear collecting section 13, and then wounded up and collected by a windup device 40. The separator st that is wound up and collected is transferred to a carry-out conveyor 41 and carried out.

[Data Recording Process]

The inspected laminated film F' having the original structure of three layers in which a new protective film p' and a new separator s' are laminated to the front and the back of the film body is introduced to the data recordation processing section 10. The defect produced position detected by the above inspection is converted to coordinate data, which is then two-dimensionally coded and recorded on the laminated film F' by a recording device 42. The recording device 42, for example, records the data (two-dimensional code) through laser printing at every predetermined pitch (e.g., 500 mm) in the film traveling direction. If the laminated film F' is divided into three in the width direction and used, the inspection data within the divided width is recorded respectively at three locations in the width direction. As dust produces with the laser printing process, a dust removing function is provided in the recording device 42.

In FIG. 4, the front surface of the laminated film F is the recording surface and the data is printed and recorded on the protective film p' positioned on the front surface side, but the back surface of the laminated film F' may serve as the recording surface by guiding the laminated film F' in a path d shown with a virtual line in FIG. 4 as necessary. In this case, the data is printed and recorded on the separator s' positioned on the back surface side.

[Laminated Film Collecting Process]

The laminated film F' subjected to the inspection and the data recordation processing is introduced to the laminated film collecting section 11, wound up and collected in a roll-form on a mount 44 set on a receiver base 43, and the original roll R' that is wound up and inspected is transferred to a conveyor 45 with the mount 44 and carried out to the outside of the device. The conveyor 45 is arranged between the laminated film collecting section 11 and the protective film supplying section 12, and is also used to carry the protective film original roll PR in.

As shown in FIG. 1, the clean room 15 accommodating the relevant device is configured to scavenge the inside of the chamber by sending a chamber clean air from an air blowing unit arranged at an appropriate location on the roof and discharging the chamber clean air from an air discharging unit arranged at an appropriate location near the floor. In particular, in the second inspecting section 5 in which the front and the back surfaces of the film body f are both exposed, the front surface side of the film body f traveling in the vertical attitude is set as the upstream side of the scavenging air flow so that foreign substances are avoided from going around the adhesive surface on the back side of the film body f and attaching thereto even if flowed on the air flow.

At an appropriate location of each processing section, a working space to which the worker can go in and out is arranged as in the first inspecting section 2, and is configured such that manual film loading operation and various manual maintenances can be performed.

Therefore, defects such as attachment of foreign substances and nicks that could not be detected due to influence of birefringence and the like can now be detected at a satisfactory accuracy by separating the protective film p and the separator s having optical characteristics from the laminated film F, and inspecting the defect site with each monitoring device of transmissive type or reflective type.

When inspecting the film body f by separating the separator from the back surface of the laminated film F(1) having an adhesive layer, the attachment of dust to the film body f is suppressed by transporting the film body f in a state where the adhesive surface does not face upward, for example, in the vertical attitude, at the same time as separating. In particular, attachment of foreign substances such as dust can be further suppressed by sending clean air from the non-adhesive surface side.

Furthermore, a new separator s' to be laminated to the adhesive surface of the film body f is transported with the laminating surface facing downward until reaching the laminating site, and thus attachment of dust to the relevant surface is suppressed. In other words, inclusion of dust to the interface of the film body f and the separator s' is suppressed.

The present invention is not limited to the above-described example, and following variants can be implemented.

(1) In the above example, the recordation process of the inspection data is performed for each original roll R', but the inspection data may be appropriately stored in a device, transmitted to a control device in the subsequent processing device, and the corresponding inspection data may be read out and used based on individual identification of each original roll R'.

(2) The recording device 42 is not limited to a laser printing type, and various printing types may be used.

(3) In the above example, only the separator s may be separated without separating the protective film p from the laminated film F. Therefore, in the first inspecting section 2 of the device embodiment, the protective film p may be set in advance to be wound around the separation roller 24 so as not to strip to realize such configuration. In other words, the film body f separated with only the separator s and subjected to inspection is performed with various marking, and then wound up and collected in a roll-form.

INDUSTRIAL APPLICABILITY

Therefore, the present invention is suitable in performing inspection of the laminated film at a satisfactory accuracy.

The invention claimed is:

1. A method for inspecting a defect of a laminated film that inspects a detect of a wounded up laminated film, the method comprising:
 a laminated film feed-out step of feeding out from an original roll a laminated film in which a protective film on a front surface of a film body and a separator on an adhesive surface on a back side of the film body are laminated together;
 a separator separation step of making a separation surface of a separator face downward at least at a separation point before separating the separator from the laminated film while guiding the fed-out laminated film to a predetermined path;
 an inspection step of inspecting presence of the defect of the laminated film while transporting the laminated film with the separation surface of the separator facing downward, and storing inspection information in a storage device;
 a separator laminating step of laminating the separator to the separation surface with the separation surface of the separator of the inspected film body facing downward; and
 a laminated film collecting step of winding up the inspected laminated film in which the separator is laminated to the back surface of the film body to form an inspected original roll.

2. The method for inspecting the defect of the laminated film according to claim 1, further comprising:

a protective film separation step of striping the protective film from the laminated film;
 an inspection step of inspecting presence of the defect on the front surface of the film body while guiding the laminated film with the protective film separated therefrom to a predetermined film travel path, and storing inspection information in the storage device; and
 a protective film laminating step of laminating a protective film to a front surface of the inspected film body; wherein
 the laminated film collecting step includes winding up the inspected laminated film in which the protective film is laminated to the front surface of the film body and the separator is laminated to the back surface of the film body to form an inspected original roll.

3. The method for inspecting the defect of the laminated film according to claim 2, wherein
 the separator is separated from the back surface of the film body and inspection is performed after separating the protective film from the film body and inspecting the resulting protective film; and
 the laminated film is wounded up to form an inspected original roll after laminating the protective film and the separator to the front surface and the back surface of the inspected film body.

4. The method for inspecting the defect of the laminated film according to claim 2 or 3, comprising a marking step of marking the defect detected site of the film body after the inspection step of the film body with the protective film separated therefrom.

5. The method for inspecting the defect of the laminated film according to claim 2 or 3, comprising a data recording step of providing position data of a detected defect site to an appropriate location on the front surface or the back surface of the inspected laminated film after at least either the separator laminating step or the protective film laminating step.

6. The method for inspecting the defect of the laminated film according to claim 2 or 3, wherein at least the inspection step is performed in a clean room.

7. The method for inspecting the defect of the laminated film according to claim 6, wherein the clean room is scavenged with the front surface side of the film as an upstream side of an air flow with respect to the film body traveling in a vertical attitude.

8. A device for inspecting a defect of a laminated film that inspects a defect of a wounded up laminated film, the device comprising:
 a laminated film supply device for supplying a laminated film in which a protective film on a front surface of a film body and a separator on an adhesive surface on a back side of the film body are laminated together;
 a separator separation device for separating the separator from the laminated film while introducing the laminated film fed out from the laminated film supply device to a predetermined path;
 an inspection device for making a separation surface of a separator face downward at least at the separation point of the separator, and inspecting presence of the defect while maintaining this state and transporting;
 a storage device for storing information of the inspection result;
 a separator supply device for feeding out a separator to a back surface of the film body;
 a separator laminating device for laminating the separator fed out from the separator supply device to the separation surface with the separation surface of the separator of the inspected film body facing downward; and a laminated film collecting device for winding up the inspected laminated film in which the separator is laminated to the back surface of the film body.

9. The device for inspecting the defect of the laminated film according to claim 8, comprising:
- a protective film separation device for separating the protective film from the laminated film;
- an inspection device for inspecting presence of the defect at the front surface of the film body while introducing the laminated film with the protective film separated therefrom to a predetermined film travel path;
- a storage device for storing information of the inspection result;
- a protective film supply device for feeding out a protective film to the front surface of the film body; and
- a protective film laminating device for laminating the protective film fed out from the protective film supply device to the front surface of the inspected film body.

10. The device for inspecting the defect of the laminated film according to claim 9, comprising a marking device for marking a defect detected site of the film body based on the inspection result after separation of the protective film.

11. The device for inspecting the defect of the laminated film according to claim 9 or 10, comprising a data recording device for providing position data of the detected defect site to an appropriate location on the front surface or the back surface of the inspected laminated film after at least either the separator lamination or the protective film lamination.

12. The device for inspecting the defect of the laminated film according to claim 9 or 10, wherein the inspection device after at least the separation of the separator is arranged in a clean room.

13. The device for inspecting the defect of the laminated film according to claim 11, wherein the inspection device after at least the separation of the separator is arranged in a clean room.

* * * * *